United States Patent
Gosselin et al.

(10) Patent No.: US 11,414,412 B2
(45) Date of Patent: Aug. 16, 2022

(54) PROCESS FOR THE PREPARATION OF A MEDICAMENT

(71) Applicant: Genentech, Inc., South San Francisco, CA (US)

(72) Inventors: Francis Gosselin, South San Francisco, CA (US); Andrew McClory, South San Francisco, CA (US); Zhigang Cheng, South San Francisco, CA (US)

( * ) Notice: Subject to any disclaimer, the term of this patent is extended or adjusted under 35 U.S.C. 154(b) by 91 days.

(21) Appl. No.: 17/016,900

(22) Filed: Sep. 10, 2020

(65) Prior Publication Data

US 2021/0070749 A1  Mar. 11, 2021

Related U.S. Application Data

(60) Provisional application No. 62/898,861, filed on Sep. 11, 2019, provisional application No. 62/934,382, filed on Nov. 12, 2019.

(51) Int. Cl.
C07D 417/14 (2006.01)

(52) U.S. Cl.
CPC .................. *C07D 417/14* (2013.01)

(58) Field of Classification Search
CPC .................................... C07D 417/14
USPC ......................................... 548/200
See application file for complete search history.

(56) References Cited

FOREIGN PATENT DOCUMENTS

| WO | 2014/048939 A1 | 3/2014 |
| WO | 2015/140189 A1 | 9/2015 |

OTHER PUBLICATIONS

Ando, T., et al., "Iodine-catalyzed aziridination of alkenes using Chloramine-T as a nitrogen source" Tetrahedron 54(44):13485-13494 (Oct. 29, 1998).
Ando, T., et al., "Nitrogen atom transfer to alkenes utilizing Chloramine-T as nitrogen source" Tetrahedron Lett 39(3-4):309-312 (Jan. 15, 1998).
Cardullo, F., et al., "Deprotection of o-Nitrobenzensulfonyl (Nosyl) Derivatives of Amines-Mediated by a Solid-Supported Thiol"SYN Lett 2005(19):2996-2998 (Dec. 1, 2005).
Champagne, P. et al., "Monofluorination of Organic Compounds: 10 Years of Innovation" Chem Rev 115(17):9073-9174 (Apr. 9, 2015).
Chang, M., et al., "N-Bromosuccinimide-mediated reaction of cyclic styrenes with chloramine-T" Tetrahedron Lett 55(34):4767-4770 (Aug. 20, 2014).
Fukuyama, T., et al., "2- and 4-Nitrobenzenesulfonamides: Exceptionally versatile means for preparation of secondary amines and protection of amines" Tetrahedron Lett 36(36):6373-6374 (Sep. 4, 1995).
Hu, X. Eric, "Nucleophilic Ring Opening of Aziridines" Tetrahedron 60(12):2701-2743 (Mar. 15, 2004).
Jeong, J. et al., "Bromine-Catalyzed Aziridination of Olefins. A Rare Example of Atom-Transfer Redox Catalysis by a Main Group Element" J Am Chem Soc 120(27):6844-6845 (Jun. 27, 1998).
Maligres, P., et al., "Nosylarizidines: Activated aziridine electrophiles" Tetrahedron Lett 38(30):5253-5256 (Jul. 28, 1997).
Nicolaou, K.C., et al., "Metathesis Reactions in Total Synthesis" Angew Chem Int Ed 44(29):4490-4527 (Jul. 18, 2005).
Wang, X., et al., "Optimization of Pan-Pim Kinase Activity and Oral Bioavailability Leading to Diaminopyrazole (GDC-03389) for the Treatment of Multiple Myeloma" J Med Chem 62(4):2140-2153 (Feb. 28, 2019).
"International Search Report—PCT/US2020/050086" (w/Written Opinion),:1-10 (dated Mar. 18, 2021).
Sureshkumar, D., et al., "Regio- and stereoselective synthesis of aziridino epoxides from cyclic dienes" J Org Chem 71(4):1653-1657 (Jan. 27, 2006).

*Primary Examiner* — Kahsay Habte
(74) *Attorney, Agent, or Firm* — Brian L. Buckwalter

(57) ABSTRACT

A process for the manufacture N-(5-((5R,6S)-5-amino-6-fluorooxepan-2-yl)-1-methyl-1H-pyrazol-4-yl)-2-(2,6-difluorophenyl)thiazole-4-carboxamide (I) wherein the vicinal amino fluoro substituents are introduced by treating 5 with sodium chloro((4-nitrophenyl)sulfonyl)amide and N-bromosuccinimide and unraveling the resulting substituted aziridine (6) with trimethylamine trihydrofluoride to afford 7 which is further processed to afford 1.

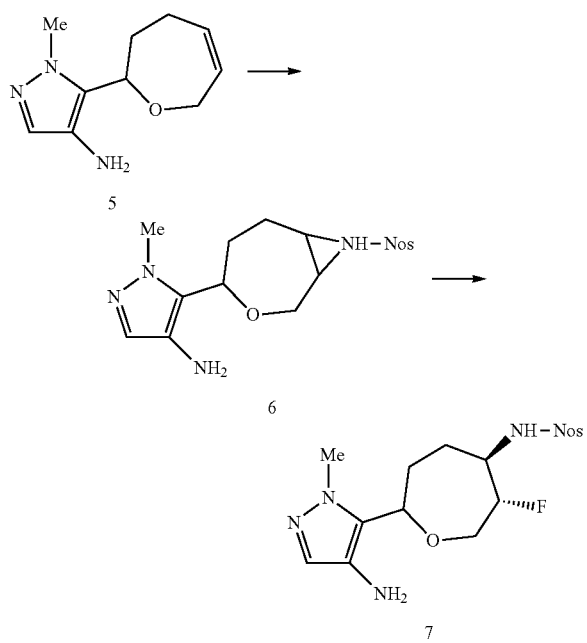

10 Claims, No Drawings

PROCESS FOR THE PREPARATION OF A MEDICAMENT

CROSS REFERENCE TO RELATED APPLICATIONS

This application claims the benefit of priority to U.S. Provisional Patent Application No. 62/934,382, filed Nov. 12, 2019 and to U.S. Provisional Patent Application No. 62/898,861, filed Sep. 11, 2019, both of which are incorporated herein by reference in its entirety.

FIELD OF THE INVENTION

The present invention relates to a new process for the preparation of a PIM kinase inhibitor of formula 1. One object of the present invention is an improved process, which can be practiced efficiently and safely on commercial scale.

BACKGROUND OF THE INVENTION

Pim kinases are family of three highly related serine and threonine protein kinases encoded by the genes Pim-1, Pim-2, and Pim-3. The gene names are derived from the phrase Proviral Insertion, Moloney, frequent integration sites for murine moloney virus wherein the insertions lead to overexpression of Pim kinases and either de novo T-cell lymphomas, or dramatic acceleration of tumorigenesis in a transgenic Myc-driven lymphoma model (Cuypers et al. (1984) Cell, vol. 37 (1) pp. 141-50; Selten et al. (1985) EMBO J. vol. 4 (7) pp. 1793-8; van der Lugt et al. (1995) EMBO J. vol. 14 (11) pp. 2536-44; Mikkers et al. (2002) Nature Genetics, vol. 32 (1) pp. 153-9; van Lohuizen et al. (1991) Cell, vol. 65 (5) pp. 737-52). These experiments reveal synergy with the oncogene c-Myc, and suggest that inhibition of the Pim kinases may have therapeutic benefit.

N-(5-((5R,6S)-5-amino-6-fluorooxepan-2-yl)-1-methyl-1H-pyrazol-4-yl)-2-(2,6-difluorophenyl)thiazole-4-carboxamide (I) is a highly selective inhibitor of Pim-1, Pim-2, and Pim-3. WO 2015/140189 discloses PIM inhibitors including 1 and related cyclic ether pyrazolyl compounds.

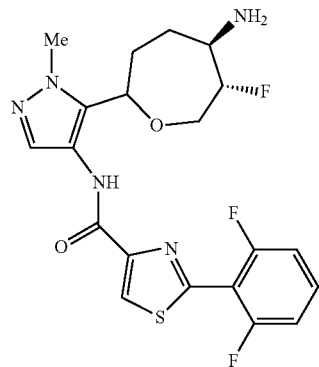

Other PIM inhibitors have been reported. (W. Blackaby et al., WO2014/048939; X. Wang et al. *J. Med. Chem.* 2019 62:2140-2153; L. S. Chen et al. *Blood* 2011 118(3):693; Dakin, L. A. et al. *Bioorg. Med. Chem. Lett.* 2012 22(14): 4599-4604 and Burger, M. T. et al., *J. Med. Chem.* 2015 58(21):8373-8386.

BRIEF SUMMARY OF THE INVENTION

The present process is an improved process for the preparation of substituted oxepane derivatives comprising the steps of treating a 2,3,4,7-tetrahydrooxepine of formula 5 with sodium chloro((4-nitrophenyl)sulfonyl)amide and N-bromosucinimide to afford the aziridine 6 which can be subjected to HF mediated ring opening to afford 7 which can be cleaved to afford fluoro-amino oxepane 8.

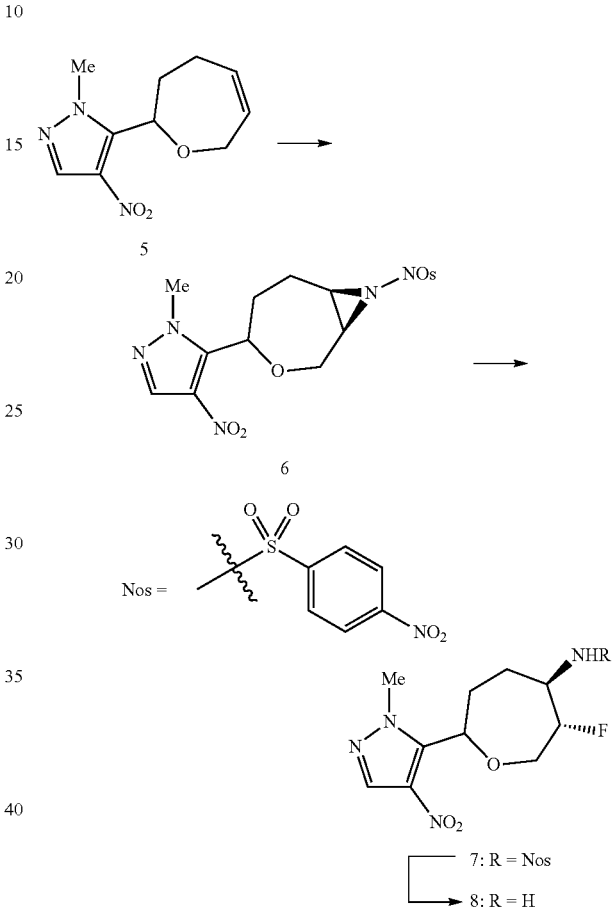

Protection of the nascent primary amine, reduction of the nitro group, condensation with 2-(2,6-difluorophenyl)thiazole-4-carboxylic acid with 1-1'-carbonyl diimidazole (CDI) and subsequent deprotection of the amine affords 1.

DETAILED DESCRIPTION OF THE INVENTION

The following definitions are set forth to illustrate and define the meaning and scope of the various terms used to describe the invention herein.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term protecting group (PG) refers to any substituent conventionally used to hinder the reactivity of a functional group. As used herein refers to a chemical group that (a) efficiently combines with a reactive group in a molecule; (b) prevents a reactive group from participating in an undesirable chemical reaction; and (c) can be easily removed after protection of the reactive group is no longer required. Protecting groups are used in synthesis to temporarily mask the characteristic chemistry of a functional group because it interferes with another reaction. Reagents and protocols for to introduce and remove protecting groups are well known and have been reviewed in numerous texts (e.g., T. W. Greene and P. G. M. Wuts, *Protective Groups in Organic Synthesis*, 3' edition, John Wiley & Sons, New York, 1999, and Harrison and Harrison et al., *Compendium of Synthetic Organic Methods*, Vols. 1-8 John Wiley and Sons, 1971-1996). One skilled in the chemical arts will appreciate that on occasion protocols must be optimized for a particular molecule and such optimization is well with the ability of one skilled in these arts.

Suitable amino protecting groups for Rare fluorenylmethyloxycarbonyl (Fmoc), carbobenzyloxy (Cbz), methoxybenzylcarbonyl (Moz), tert-butoxycarbonyl (Boc), trichloroethoxycarbonyl (Troc), 2-(trimethylsilyl)ethoxycarbonyl (Teoc) or vinyloxycarbonyl (Voc). A preferred amino protecting group, as defined for $R^1$ is Boc.

The term "halogen" refers to fluorine, chlorine, bromine and iodine.

Conversion of olefins to aziridines with chloramine T, or other N-chloro arylsulfonamides in the presence of bromine sources (Other bromine sources can be employed. e.g., $ZnBr_2$, $HgBr_2$, $FepBr_2$, $CuBr_2$, NBS and phenyltrimethylammonium tribromide have been reported (Jeong, J. U. et al. *J. Am. Chem. Soc.* 1998 120:6844; Ando, T. et al. *Tetrahedron Lett.* 1998 39:309; Ando, T. et al. *Tetrahedron* 1998 54:13485; Chang, M.-Y. et al. *Tetrahedron Lett.* 2014 55:4767). One skilled in the art will appreciate that in introduction of the aziridine can be accomplished with other sodium chloro(arylsulfonyl)amides. ortho-Nitrophenyl and para-nitrophenyl N-chloro arylsulfonamides can be used advantageously since they can be hydrolyzed with thiols and potassium tert-butoxide. N-chloro tert-butylsulfonamide affords aziridines substituted bearing a t-butylsulfonamide moiety which can be cleaved with trifluoromethylsulfonic acid. Ring opening of aziridines by nucleophilic fluorides to afford beta-fluoro amines have also been reported. (Hu, E. Eric, *Tetrahedron* 2004 60:2701-2743; Champagne, P. R. et al. *Chemical Rev.* 2015 113:9073-9174.)

Reduction of a nitro group to an amine can be accomplished with a metal reducing agent such as Fe, Sn or Zn, in a reaction inert solvent, e.g. MeOH, EtOH, EtOAc, benzene, toluene, xylene, o-dichlorobenzene, DCM, DCE, THF, dioxane, or mixtures thereof. If desired, when the reducing reagent is Fe, Sn or Zn, the reaction is carried out under acidic conditions in the presence of water. The reduction may be carried out by hydrogenation in the presence of a metal catalyst, e.g. nickel catalysts such as Raney nickel, palladium catalysts such as Pd/C, platinum catalysts such as $PtO_2$, or ruthenium catalysts such as $RuCl_2(Ph_3P)_3$ under $H_2$ atmosphere or in the presence of hydrogen sources such as hydrazine or formic acid. If desired, the reaction is carried out under acidic conditions, e.g., in the presence of HCl or HOAc.

Carboxylic acids can be can be activated with agents such as EDC, DCC, benzotriazol-1-yloxy-tris(dimethylamino) phosphonium hexafluorophosphate (BOP), bromo-tris-pyrrolidinophosphonium hexafluorophosphate (PyBrOP), or 2-fluoro-1-methylpyridinium p-toluenesulphonate (Mukaiyama's reagent with or without a base such NMM, TEA or DIPEA in an inert solvent such as dimethylformamide (DMF) or dichloromethane at temperatures between 0° C. and 60° C. Acylation of amines (J. March, supra pp. 417-425; H. G. Benz, *Synthesis of Amides and Related Compounds in Comprehensive Organic Synthesis*, E. Winterfeldt, ed., vol. 6, Pergamon Press, Oxford 1991 pp. 381-411; see R. C. Larock, *Comprehensive Organic Transformations-A Guide to Functional Group Preparations*, 1989, VCH Publishers Inc., New York; pp. 972-976) has been reviewed.

In one embodiment of the invention there is provided a process for the preparation of 1 comprising the steps of (i) treating 1-methyl-4-nitro-5-(2,3,4,7-tetrahydrooxepin-2-yl)-1H-pyrazole (5, Blackaby, W. et al., WO2014/048939) with an N-chlorosulfonamide (18; $R^1$ is nitrophenyl or tert-Bu) and a bromine source to afford the aziridine 19; (ii) treating 19 with a nucleophilic fluoride to afford 20a; (iii) removing the amino protecting group ($R^1$) to afford 8; (iv) introducing a second

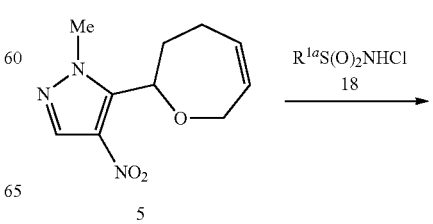

5

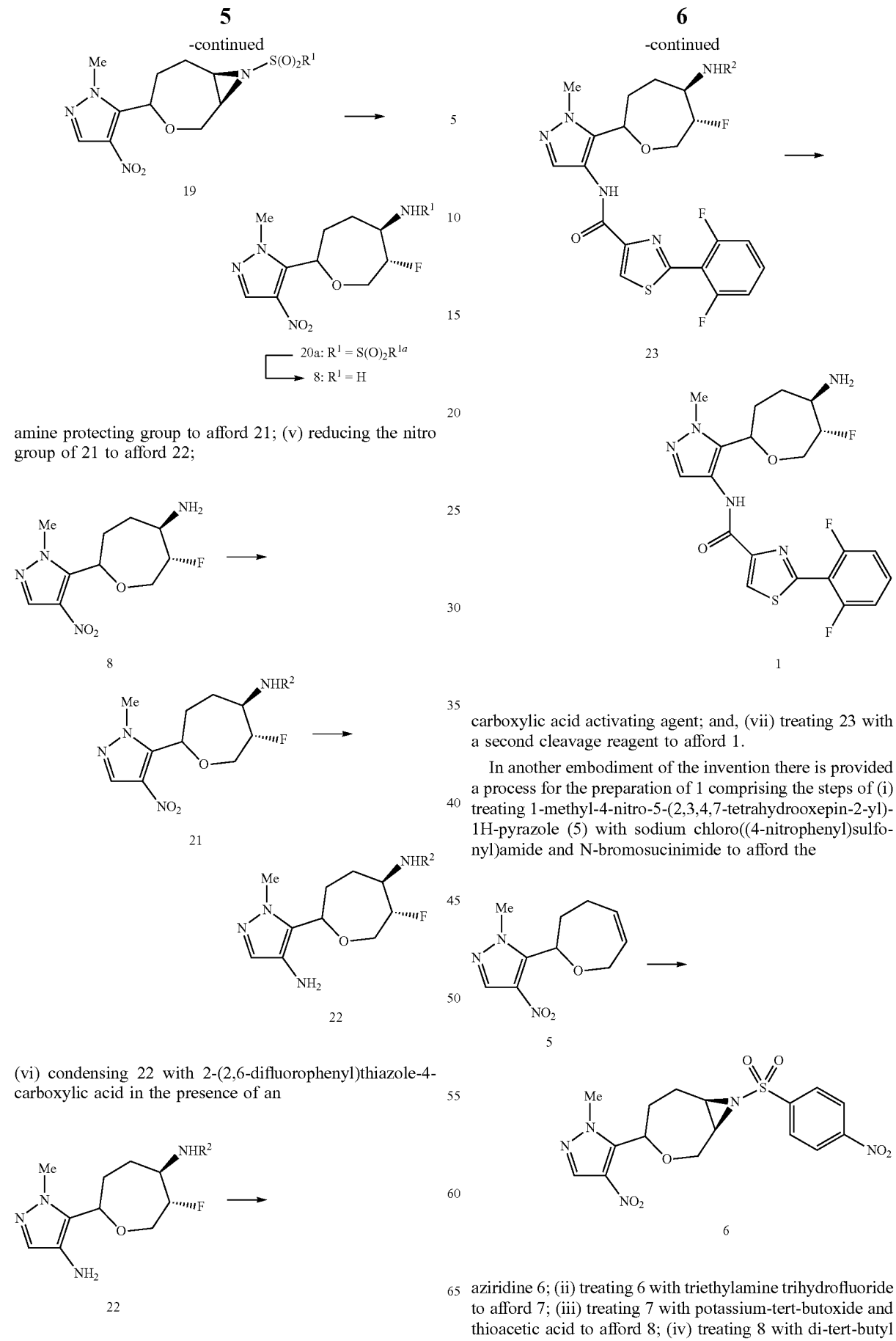

amine protecting group to afford 21; (v) reducing the nitro group of 21 to afford 22;

(vi) condensing 22 with 2-(2,6-difluorophenyl)thiazole-4-carboxylic acid in the presence of an carboxylic acid activating agent; and, (vii) treating 23 with a second cleavage reagent to afford 1.

In another embodiment of the invention there is provided a process for the preparation of 1 comprising the steps of (i) treating 1-methyl-4-nitro-5-(2,3,4,7-tetrahydrooxepin-2-yl)-1H-pyrazole (5) with sodium chloro((4-nitrophenyl)sulfonyl)amide and N-bromosucinimide to afford the aziridine 6; (ii) treating 6 with triethylamine trihydrofluoride to afford 7; (iii) treating 7 with potassium-tert-butoxide and thioacetic acid to afford 8; (iv) treating 8 with di-tert-butyl

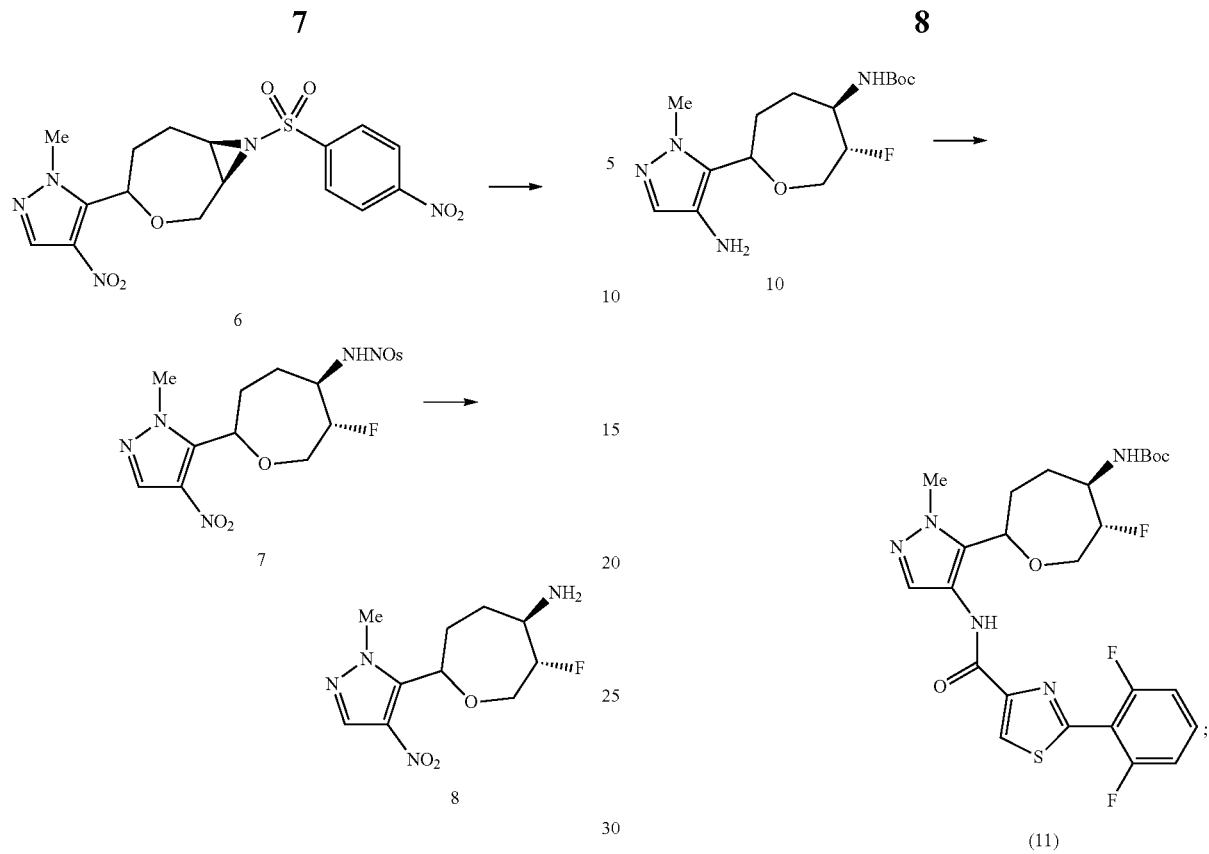

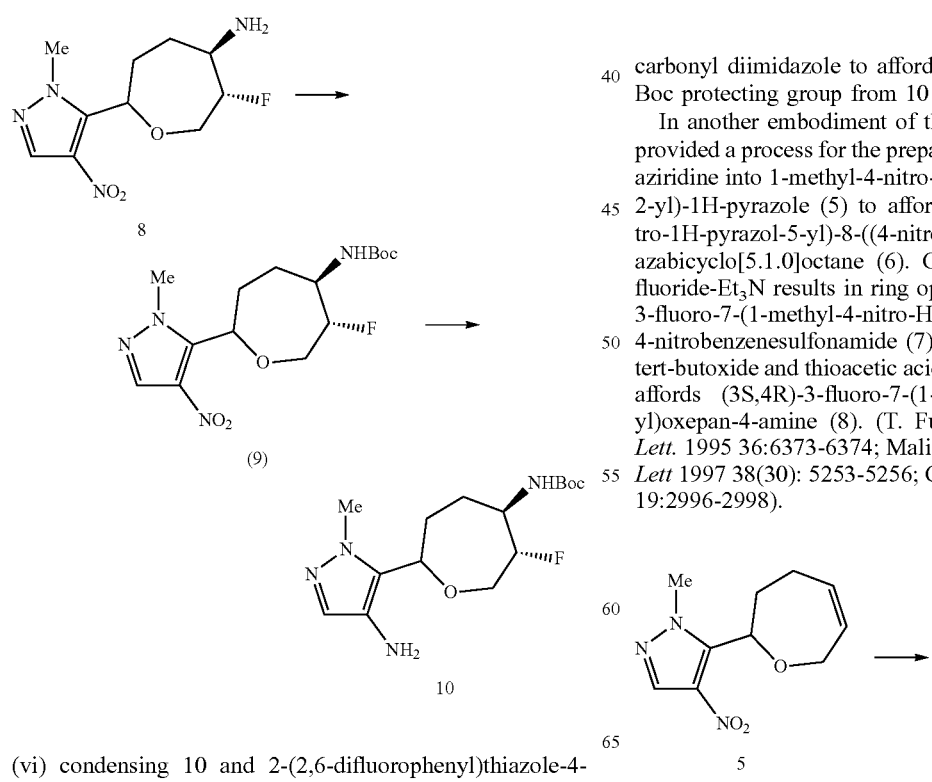

pyrocarbonate to afford 9; (v) reducing 9 with hydrogen and Noblyst P8078 in ethanol to afford 10;

(vi) condensing 10 and 2-(2,6-difluorophenyl)thiazole-4-carboxylic acid in the presence of carbonyl diimidazole to afford 11; and, (vii) removing the Boc protecting group from 10 to afford 1.

In another embodiment of the present invention there is provided a process for the preparation of 8 by introducing an aziridine into 1-methyl-4-nitro-5-(2,3,4,7-tetrahydrooxepin-2-yl)-1H-pyrazole (5) to afford (1R,7R)-4-(1-methyl-4-nitro-1H-pyrazol-5-yl)-8-((4-nitrophenyl)sulfonyl)-3-oxa-8-azabicyclo[5.1.0]octane (6). Contacting 6 with hydrogen fluoride-Et$_3$N results in ring opening to afford N-((3S,4R)-3-fluoro-7-(1-methyl-4-nitro-H-pyrazol-5-yl)oxepan-4-yl)-4-nitrobenzenesulfonamide (7). Reacting 7 with potassium tert-butoxide and thioacetic acid cleaves the Nos moiety and affords (3S,4R)-3-fluoro-7-(1-methyl-4-nitro-H-pyrazol-5-yl)oxepan-4-amine (8). (T. Fukuyama et al. *Tetrahedron Lett.* 1995 36:6373-6374; Maligres, P. M. et al. *Tetrahedron Lett* 1997 38(30): 5253-5256; Cardullo, F. et al *Synlett* 2005 19:2996-2998).

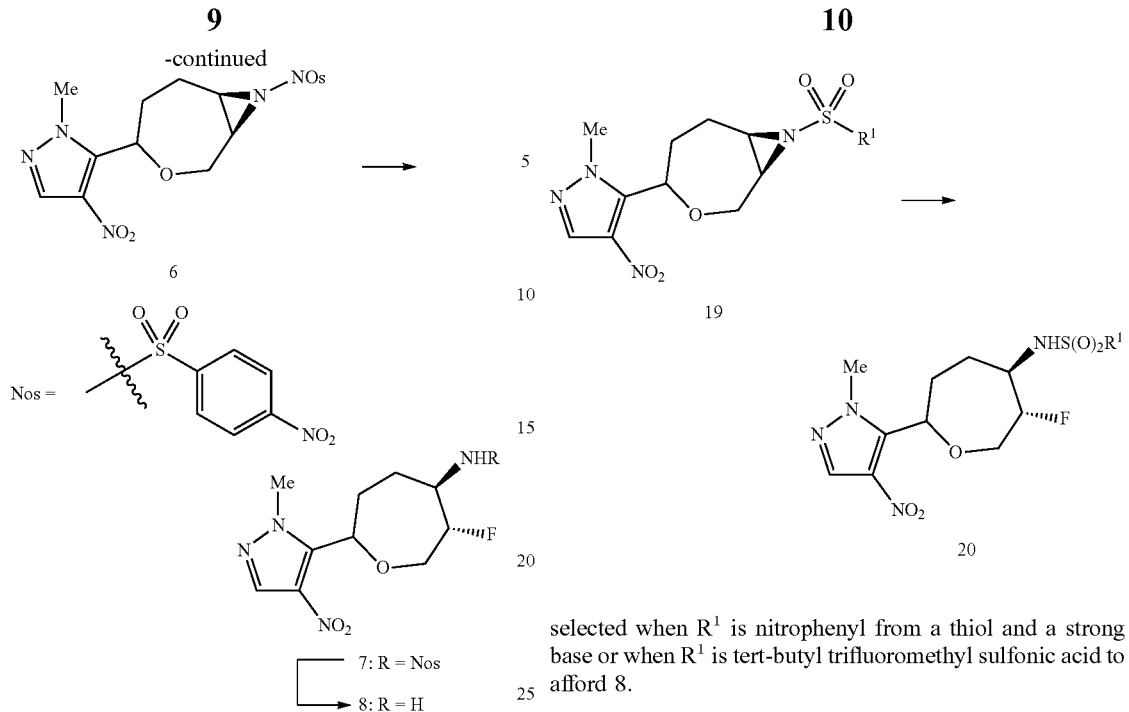

selected when R¹ is nitrophenyl from a thiol and a strong base or when R¹ is tert-butyl trifluoromethyl sulfonic acid to afford 8.

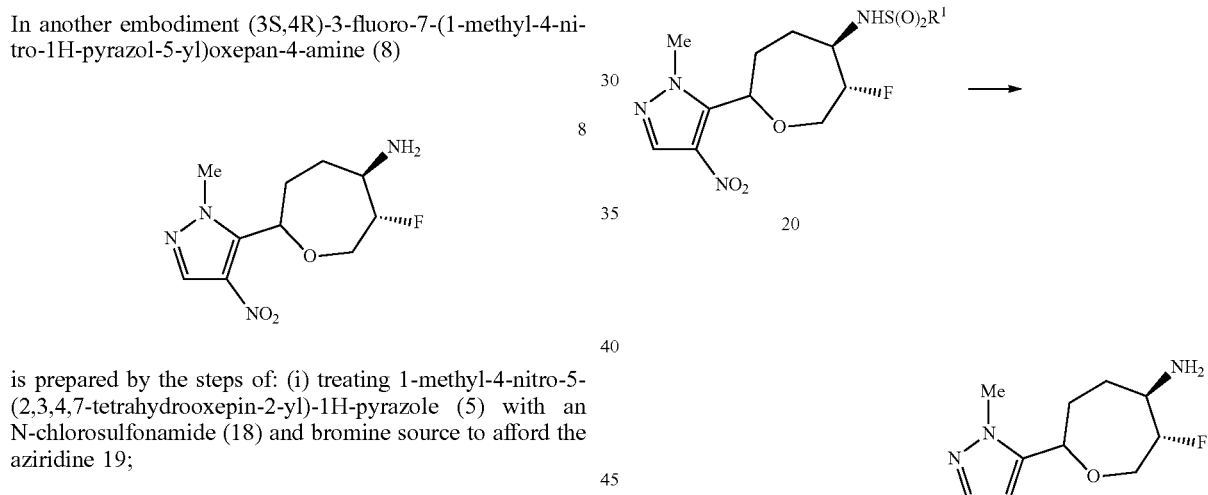

In another embodiment an N-chlorosulfonamide is sodium chloro((4-nitrophenyl)sulfonyl)amide, the bromine source is NBS, the fluoride source is triethylamine trihydrofluoride, the sulfonamide is cleaved with potassium-tert-butoxide and thioacetic acid.

In another embodiment of the invention the amino group of 8 is protected with Boc and then the nitro is reduced by catalytic hydrogenation to afford tert-butyl ((3S,4R)-7-(4-amino-1-methyl-1H-pyrazol-5-yl)-3-fluorooxepan-4-yl)carbamate (10). Acylation of 10 with 2-(2,6-difluorophenyl) thiazole-4-carboxylic acid (17) and 1,1'-carbonyl diimidazole affords 11.

In another embodiment (3S,4R)-3-fluoro-7-(1-methyl-4-nitro-1H-pyrazol-5-yl)oxepan-4-amine (8)

is prepared by the steps of: (i) treating 1-methyl-4-nitro-5-(2,3,4,7-tetrahydrooxepin-2-yl)-1H-pyrazole (5) with an N-chlorosulfonamide (18) and bromine source to afford the aziridine 19;

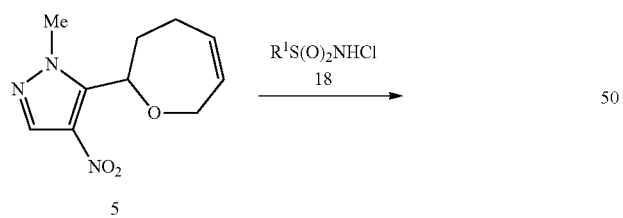

(ii) treating 19 with a nucleophilic fluoride source to afford 20; (iii) contacting 20 with a reagent

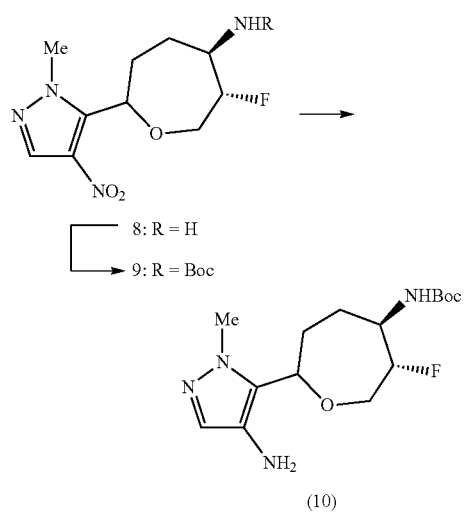

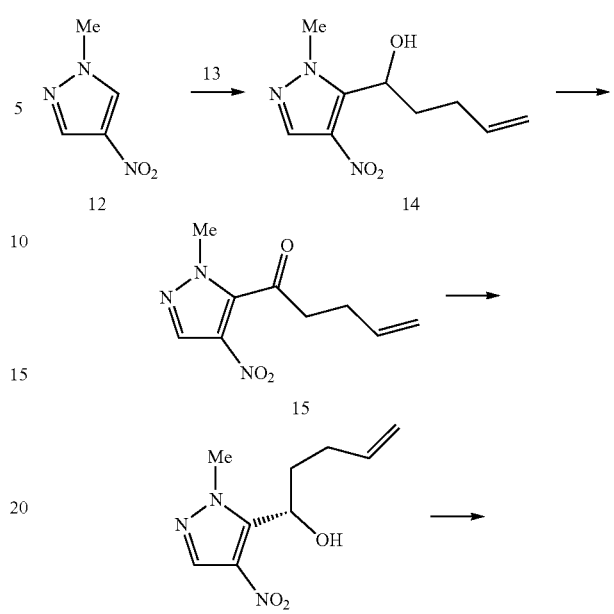

In another embodiment of the present invention 9 is resolved by chiral HPLC on CHIRALPAK AD-H to afford 9a and 9b. The enantiomer 9a can then be transformed analogously to afford 1a.

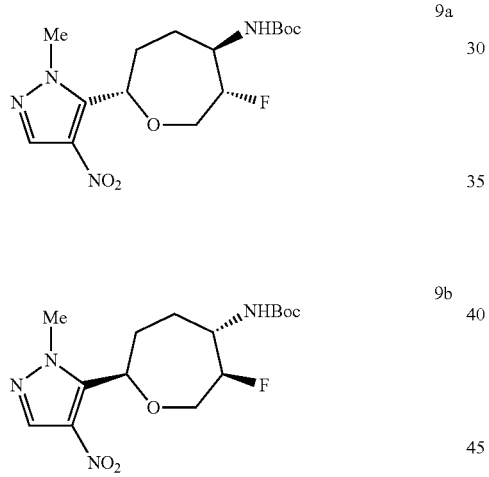

In yet another embodiment of the invention (S)-1-methyl-4-nitro-5-(2,3,4,7-tetrahydrooxepin-2-yl)-1H-pyrazole (5a) is prepared deprotonation N-methyl 4-nitro-1H-pyrazole (12) with strong base to afford (1-methyl-4-nitro-1H-pyrazol-5-yl) lithium which is condensed with pent-4-enal (13) to afford 14. Oxidation of 14 to affords the corresponding ketone 15 which is subjected to asymmetric hydrogenation with chloro{N-[(1S,2S)-2-[(R)-[2-[[1,2,3,4,5,6-η)-4-methylphenyl]methoxy]ethyl]amino]-1,2-diphenylethylmethanesulfonamidato}ruthenium(II) to afford 14a in 98% yield and 94% ee. The chiral alcohol is alkylated with allyl bromide to afford (S)-1-(1-methyl-4-nitro-1H-pyrazol-5-yl)pent-4-en-1-ol (16) which is converted to (S) 1-methyl-4-nitro-5-(2,3,4,7-tetrahydrooxepin-2-yl)-1H-pyrazole (5a) by olefin metathesis (for reviews of the olefin metathesis reaction see, for example, K. C. Nicolaou et al., *Angew. Chem. Int. Ed.* 2005 44:4490; A. Michrowska and K. Grela, *Pure Appl. Chem.* 2008 80(1): 31).

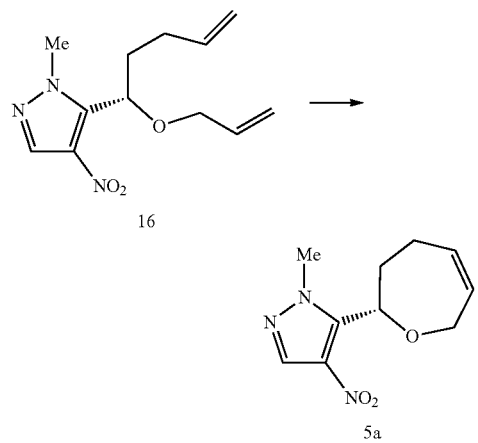

Example 1

(1R,7R)-4-(1-methyl-4-nitro-1H-pyrazol-5-yl)-8-((4-nitrophenyl)sulfonyl)-3-oxa-8-azabicyclo[5.1.0]octane (6)

A 500 L reactor was charged with acetonitrile (200 kg). The reactor was then charged with 1-methyl-4-nitro-5-(2,3,4,7-tetrahydrooxepin-2-yl)-1H-pyrazole (25 kg, 112 mol) and N-bromosuccinimide (4 kg, 22.5 mol) and the resulting suspension was stirred until the solution was homogenous. The reactor was purged with $N_2$ and the reaction mixture was maintained between 20 and 30° C. To the solution was added in 4 batches sodium chloro((4-nitrophenyl)sulfonyl) amide (43.4 kg 168 mol) while maintaining a positive $N_2$ pressure to maintain an inert atmosphere. The reaction was stirred for 13 h and then $H_2O$ (1000 L) was charged. The resulting mixture was stirred for 1 h and the resulting slurry was collected by filtration. The solid was slurried with EtOH (250 kg) filtered and centrifuged to afford (1R,7R)-4-(1-methyl-4-nitro-1H-pyrazol-5-yl)-8-((4-nitrophenyl)sulfonyl)-3-oxa-8-azabicyclo[5.1.0]octane (6) as a white solid. The solid was dried in vacuo to afford 42 kg, 88.6% isolated yield as a white powder.

Example 2

N-((3S,4R)-3-fluoro-7-(1-methyl-4-nitro-1H-pyrazol-5-yl)oxepan-4-yl)-4-nitrobenzenesulfonamide (7)

To a 1000 L reactor was charged with MeCN (168 kg) and THF (168 kg) was added with stirring (1R,7R)-4-(1-methyl-4-nitro-1H-pyrazol-5-yl)-8-((4-nitrophenyl)sulfonyl)-3-oxa-8-azabicyclo[5.1.0]octane (6; 42 kg, 99.3 mol) and $Et_3N$—$(HF)_3$ (31.9 kg, 267.9 mol). The reactor was maintained at 20 to 30° C. and DBU (45.2 kg, 297.9 mol) was added dropwise. The reactor was purged with $N_2$ and the reaction heated to 65-70° C. for 20 h under positive $N_2$ pressure. The reaction mixture was cooled to 20-30° C. and the reaction quenched with 1M HCl (47.0 kg). The solvents were removed by vacuum distillation (internal temperature <50° C.) and the resulting solid was filtered sequentially slurried with $H_2O$ (RT), DCM (RT) and thrice with MeCN (80° C.). The solid was filtered and dried in vacuo at 45° C. to afford 7 (17 kg, 38.6% isolated) as an off white solid.

Example 3

(3S,4R)-3-fluoro-7-(1-methyl-4-nitro-1H-pyrazol-5-yl)oxepan-4-amine (8)

A 500 L reactor was charges with MeOH (250 kg) and maintained under a N2 atmosphere. Potassium tert-butoxide (24.3 kg, 36.1 mol) was added portionwise at 20 to 30° C. To the resulting solution was added dropwise $HSCH_2CO_2H$ (12.5 kg, 135.9 mol) while maintaining the solution at 20 to 30° C. The resulting solution was stirred for at RT for 1 h then 7 (16 kg, 36.1 mol) was added. The reaction mixture was heated at 45-60° C. for about 4 h. The reaction mixture was quenched with $H_2O$ (320 kg) and the MeOH distilled under reduced pressure (internal temperature <50° C.). The aqueous phase was extracted with DCM (2×200 kg) and the combined DCM extracts washed sequentially with 0.1 M NaOH (2×100 kg) and $H_2O$ (100 kg) then dried ($Na_2SO_4$), filtered and the DCM was replaced with petroleum ether (10 L). The resulting precipitate was filtered and air-dried to afford 8 (8.4 kg, 90%) as a white crystalline solid.

Example 4 tert-butyl ((3S,4R)-7-(4-amino-1-methyl-1H-pyrazol-5-yl)-3-fluorooxepan-4-yl)carbamate (9)

A 20 L reactor was charged with 8 (800 g, 3.10 mol), 2-Me-THF (5 L) and 1M $K_3PO_4$ (9.3 L, 9.3 mol). To the solution was added dropwise at 20-300° C. a solution of $(Boc)_2O$ (706 g, 3.25 mol) and 2-Me-THF (1 L). The resulting mixture was stirred at RT for 2 h. After the reaction was complete the organic phase was separated and the aqueous phase was extracted with DCM (3 L). The organic phase was dried ($Na_2SO_4$), filtered and concentrated. Eight identical batches were combined and concentrated to ca. 10 L and petroleum ether (10 L) was added and the resulting mixture stirred for 20 min. The resulting precipitate was collected and air-dried to afford 8 kg of 9 as a white solid.

The 7.5 kg of racemate was resolved by chiral HPLC on a 0.46 cm ID×15 cm CHIRALPAK AD-H column to afford 3.4 kg of tert-butyl ((3S,4R,7S)-3-fluoro-7-(1-methyl-4-nitro-1H-pyrazol-5-yl)oxepan-4-yl)carbamate (9a) and 3.6 kg of tert-butyl ((3R,4S,7R)-3-fluoro-7-(1-methyl-4-nitro-1H-pyrazol-5-yl)oxepan-4-yl)carbamate (9b).

Example 5 tert-butyl ((3S,4R)-7-(4-amino-1-methyl-1H-pyrazol-5-yl)-3-fluorooxepan-4-yl)carbamate (10)

A 10 L autoclave equipped with a mechanical stirrer and thermometer was charged with EtOH (7 L), tert-butyl ((3S,4R,7S)-3-fluoro-7-(1-methyl-4-nitro-1H-pyrazol-5-yl)oxepan-4-yl)carbamate (9a, 750 g, 2.09 mol) and Noblyst P8078 catalyst (37.5 g). The autoclave was closed, thrice purged with $N_2$ the thrice purged with $H_2$. The mixture was stirred at 500° C. under 2 MPa of $H_2$ pressure. The mixture was filtered through CELITE© and washed with MeOH (4 L). The filtrate was concentrated under reduced pressure to about 1 L. Four 750 g batches were combined and deionized $H_2O$ (9 L) at 50° C. for 1 h then cooled to RT. The mixture was filtered and cake washed with deionized water. The resulting solid was slurried with petroleum ether. The resulting solid was filtered and dried in vacuo at 500° C. to afford 10 (93%) as a white solid.

Example 6 tert-butyl((3S,4R)-7-(4-(2-(2,6-difluorophenyl)thiazole-4-carboxamido)-1-methyl-1H-pyrazol-5-yl)-3-fluorooxepan-4-yl)carbamate

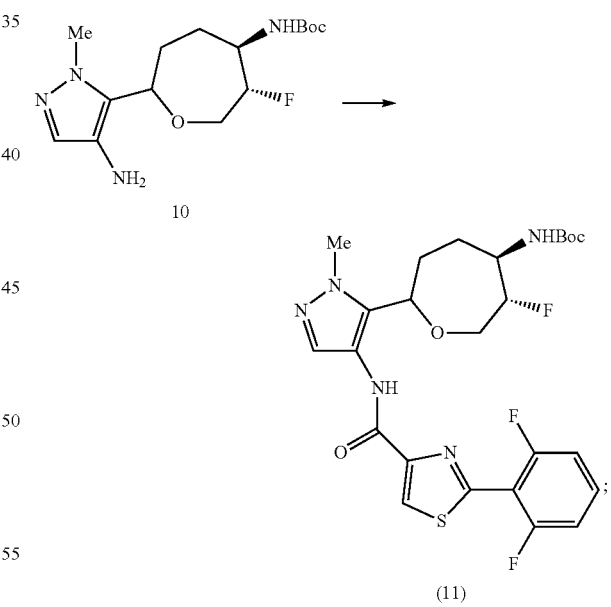

A 100 L reactor was charged with 2-(2,6-difluorophenyl) thiazole-4-carboxylic acid (17, 2.921 kg, 1.19 equiv) and THF (11.05 kg, 4.41 vol). A 20 L reactor was charged with 1,1'-carbonyldiimidazole (CDI, 1.490 kg, 1.20 equiv) and THF (13.40 kg, 5.34 vol). The contents of the 20 L reactor were transferred to the 100 L reactor over ≥15 min. The 20 L reactor was rinsed with additional THF (3.25 kg, 1.30 vol) and transferred to the 100 L reactor. The mixture was aged for about 30 min. The 20 L reactor was then charged with tert-butyl ((3S,4R)-7-(4-amino-1-methyl-1H-pyrazol-5-yl)-3-fluorooxepan-4-yl)carbamate (2.508 kg, 1.00 equiv) and THF (13.35 kg, 5.32 vol). The 20 L reactor was rinsed with THF (3.30 kg) and the solution transferred to the 100 L reactor and aged for approximately 30 min. The contents were distilled while maintaining the batch temperature ≤55° C. until approximately 20 L remained. A 50 L reactor was charged with purified water (40 kg) and NaOH (50 wt %, aq, 0.824 kg, 1.35 equiv). The contents of the 50 L reactor were transferred to the 100 L reactor over about 5 min. The contents were heated to 50° C., maintained at that temperature for at least 30 min, and then cooled to 20° C. over at least 2 h. The mixture was held for ≥60 min. The mixture was filtered through a filter dryer. The 50 L reactor was charged with purified water (9.85 kg, 3.93 vol) and NaOH (50 wt %, aq, 0.211 kg, 0.35 equiv), and the contents were transferred to the 100 L reactor, then filtered through the filter Dryer. The cake was washed with purified water until the filtrate pH was ≤7 (32.95 kg, 13.14 vol followed by 15.35 kg, 6.12 vol). After no more filtrate could be collected from the filter, the cake was dried in the filter dryer at 60° C. (jacket temperature) under house vacuum with a nitrogen purge. Drying was continued for about 3 h to afford 3.797 kg 11 (90% yield; >99.9 area % by HPLC) as an off-white solid.

Example 7

N-(5-((5R,6S)-5-amino-6-fluorooxepan-2-yl)-1-methyl-1H-pyrazol-4-yl)-2-(2,6-difluorophenyl)thiazole-4-carboxamide (I)

A 50 L reactor was charged with purified water (12.15 kg, 3.24 vol) and cooled to 10° C. Sulfuric acid (95-98 wt %, aq, 5.95 kg, 8.76 equiv) was added while maintaining the temperature less 50° C. A 100 L reactor was charged with 11 (3.747 kg, 1.00 equiv) and anisole (18.15 kg, 4.84 vol). The contents of the 50 L reactor were transferred to the 100 L reactor while maintaining the temperature less than 55° C. The contents of the 100 L reactor were heated to 55° C. and then held at that temperature for at least 60 min. The contents were cooled to 20° C. and the layers were drained into separate carboys. The aqueous layer was charged to the 100 L reactor, cooled to 10° C., and then NaOH (50 wt. %, aq, 10.10 kg, 18.6 equiv) was added while maintaining the temperature below 40° C. Anisole (17.95 kg, 4.79 vol) was charged to the 100 L reactor, and the contents were heated to 55° C. The lower aqueous layer was drained at this temperature. Purified water (14.90 kg, 3.98 vol) was added to the 100 L reactor, the contents were heated to 55° C., and then the lower organic layer was transferred to the 50 L reactor.

Anisole (5.30 kg, 1.41 vol) was charged to the 50 L reactor and the contents were distilled until 17 L remained, while maintaining the batch temperature less below 90° C. The contents were then cooled to 55° C.

The contents were heated to 85° C., and then transferred to a new 100 L reactor through an in-line filter. The 50 L reactor was charged with anisole (3.05 kg, 0.81 vol), which was then transferred to the new 100 L reactor through the in-line filter. Heptane (4.95 kg, 1.32 vol) was charged to the new 100 L reactor through an in-line filter, and the contents were heated to 90° C. The contents were agitated for at least 10 min (until a solution was obtained) and then cooled to 75° C. A slurry of 1 seeds (0.0218 kg) in anisole (0.1856 kg, 0.50 vol) were charged to reactor 3. The contents were held at 75° C. for at least 60 min, cooled to 10° C. over ≥5 h, then held at that temperature for ≥3 h. The contents were filtered through a filter dryer. Anisole (3.20 kg, 0.85 vol) and heptane (1.07 kg, 0.29 vol) were charged through an in-line filter to reactor 3, and then filtered through the filter dryer. The cake was washed with heptane (5.70 kg, 1.52 vol) and then dried in the filter dryer at 70±5° C. (jacket temperature) under house vacuum with a nitrogen purge. Drying was continued for ≥6 h. The process afforded 2.706 kg of 1 (88% yield; 99.9 area % by HPLC) as an off-white solid. The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A process for the preparation of N-(5-((5R,6S)-5-amino-6-fluorooxepan-2-yl)-1-methyl-1H-pyrazol-4-yl)-2-(2,6-difluorophenyl)thiazole-4-carboxamide (1) comprising the steps of:

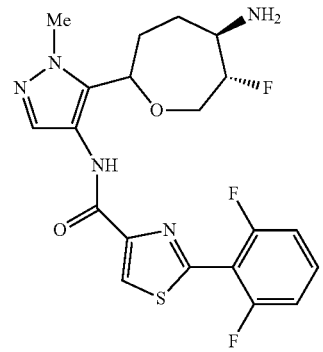

(i) treating 1-methyl-4-nitro-5-(2,3,4,7-tetrahydrooxepin-2-yl)-1H-pyrazole (5) with an N-chlorosulfonamide (18) and a bromine source to afford the aziridine 19

(i) treating 5 with R¹S(O)₂NHCl 18 to afford 19

(ii) treating 19 with a nucleophilic fluoride source to afford 20

(iii) contacting 20 with a first cleavage reagent selected from a thiol and strong base or trifluoromethyl sulfonic acid to afford 8

(iv) introducing a amine protecting group to afford 21

(v) reducing 21 to afford 22

(vi) condensing 22 with 2-(2,6-difluorophenyl)thiazole-4-carboxylic acid in the presence of an activating agent to afford 23

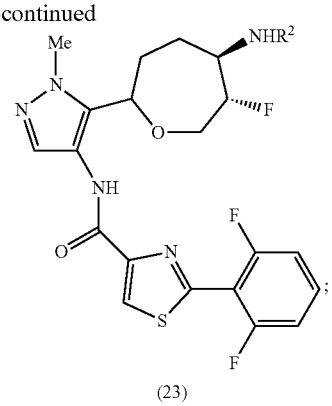

(23)

(vii) treating 23 with a second cleavage reagent to afford 1.
2. The process of claim 1 wherein;
(a) R¹ is nitrophenyl or tert-butyl;
(b) the bromine source is N-bromosuccinimide;
(c) the nucleophilic fluoride source is triethylamine tri-hydrofluoride
(d) R² is selected from the group consisting of Boc, Fmoc and Cbz;
(e) the first cleavage reagent is thioacetic acid and potassium tert-butoxide when R¹ is nitrophenyl and trifluoromethyl sulfonic acid when R¹ is tert-butyl;
(f) the nitro reducing agent is hydrogen and Noblyst P8078;
(g) the second cleavage agent is trifluoroacetic acid, piperidine or catalytic hydrogenation.
3. The process of claim 2 wherein:
(a) R¹ is p-nitrophenyl or o-nitrophenyl;
(b) R² is Boc;
(c) the first cleavage reagent is thioacetic acid and potassium tert-butoxide;
(e) the second cleavage agent is trifluoroacetic.
4. The process of claim 3 wherein R¹ is p-nitrophenyl.
5. The process of claim 1 which process further comprises the steps of
(i) deprotonating N-methyl 4-nitro-1H-pyrazole (12) with lithium hexamethyldisilazane and reacting the resulting conjugate base with pent-4-enal (13) to afford 14

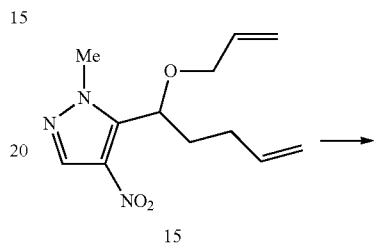

(ii) alkylating the hydroxyl moiety with allyl bromide to afford 15

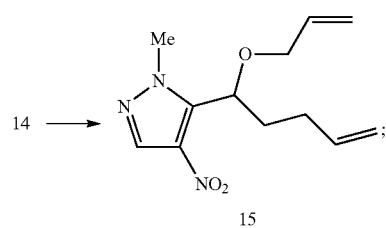 [SMILES: C=CCCC(OCC=C)c1c([N+](=O)[O-])cnn1C]

(iii) subjecting 15 to an olefin metathesis reaction to afford 5

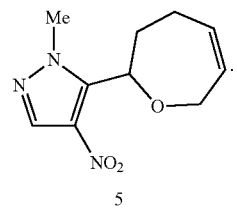

6. The process of claim 3 said process further comprising resolution of compound 9a by chiral HPLC

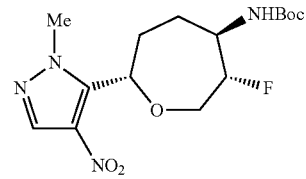

chromatography to afford 9a that is further converted into 1a as described in claim 1.
7. The process of claim 1 said process further comprising the chiral synthesis of 17 by oxidation of

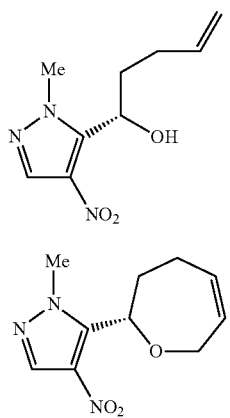

14 to afford 1-(1-methyl-4-nitro-1H-pyrazol-5-yl)pent-4-en-1-one (16) with the Dees-Martin reagent and chiral catalytic hydrogenation with chloro[N-[(1R,2R)-1,2-diphenyl-2-[[3-($\eta^6$-phenyl)propyl]amino-κN]ethyl]-4-methylbenzenesulfonamidato-κN]-ruthenium to afford (S)-1-methyl-4-nitro-5-(2,3,4,7-tetrahydrooxepin-2-yl)-1H-pyrazole (17) which is further transformed to 1 as described in claim 1.

8. The process of claim 6 wherein the N-chlorosulfonamide is sodium chloro((p-nitrophenyl)sulfonyl)amide, and the cleavage reagent, the cleavage reagent is thioacetic acid and potassium tert-butoxide.

9. The process of claim 6 wherein the N-chlorosulfonamide is sodium chloro(o-nitrophenyl)sulfonyl)amide, and the cleavage reagent, the cleavage reagent is thioacetic acid and potassium tert-butoxide.

10. The process of claim 6 wherein the N-chlorosulfonamide is sodium chloro(tert-butylsulfonyl)amide and the cleavage reagent trifluoromethylsulfonic acid.

* * * * *